United States Patent [19]

Tartof

[11] Patent Number: 5,196,328
[45] Date of Patent: Mar. 23, 1993

[54] MODIFIED CLONING VECTORS FOR RESTRICTION MAPPING, THEIR PREPARATION AND USE

[75] Inventor: Kenneth D. Tartof, Jenkintown, Pa.

[73] Assignee: Institute for Cancer Research, Philadelphia, Pa.

[21] Appl. No.: 52,799

[22] Filed: May 21, 1987

[51] Int. Cl.[5] .................. C07H 17/00; C12P 19/34
[52] U.S. Cl. ........................ 435/172.3; 435/5; 435/6; 435/29; 435/320.1; 536/27; 935/26; 935/29; 935/31; 935/78
[58] Field of Search ............... 435/5, 6, 29, 172.3, 435/320.1; 536/27; 935/26, 29, 31, 78

[56] References Cited

U.S. PATENT DOCUMENTS 4,293,652 10/1981 Cohen .................................. 435/172

FOREIGN PATENT DOCUMENTS 0076696 4/1983 European Pat. Off.

OTHER PUBLICATIONS

Bethesda Research Labs. *Catalogue & Reference Guide* (1985) p. 52 and Section 12, pp. 117–149.
Gibson et al. (1987) Gene, vol. 53, pp. 283–286.
Norrander et al. (1983) Gene, vol. 26, pp. 101–106.
Poustka et al. (1986) Trends in Genetics, vol. 2, pp. 174–179.
Walh et al., *Proc. Natl. Acad. Sci.*, 84:2160 (1987).
Poustka et al., *Nature*, 325:353 (1987).
Smith and Birnsteil, *Nucl. Acids Research*, 3:2387 (1976).
Jones et al., *Nucl. Acids Research*, 11:3919 (1983).
Jeang et al., *J. Virology*, 48:135 (1983).
Adldinger et al., *Virology*, 141:221 (1985).
Hayward et al., *J. Virology*, 43:201 (1982).
Laux et al., *J. Virology*, 56:987 (1985).
Abrecht et al., *J. Virology*, 56:466 (1985).

Primary Examiner—Amelia Burgess Yarbrough
Assistant Examiner—Ardin H. Marschel
Attorney, Agent, or Firm—Dann, Dorfman, Herrell and Skillman

[57] ABSTRACT

Modified cloning vectors having general utility for easily obtaining unambiguous restriction maps of recombinant DNA molecules and the methods of preparation and use of such vectors.

13 Claims, 4 Drawing Sheets

FIG.4A  B H X Sl S Xb
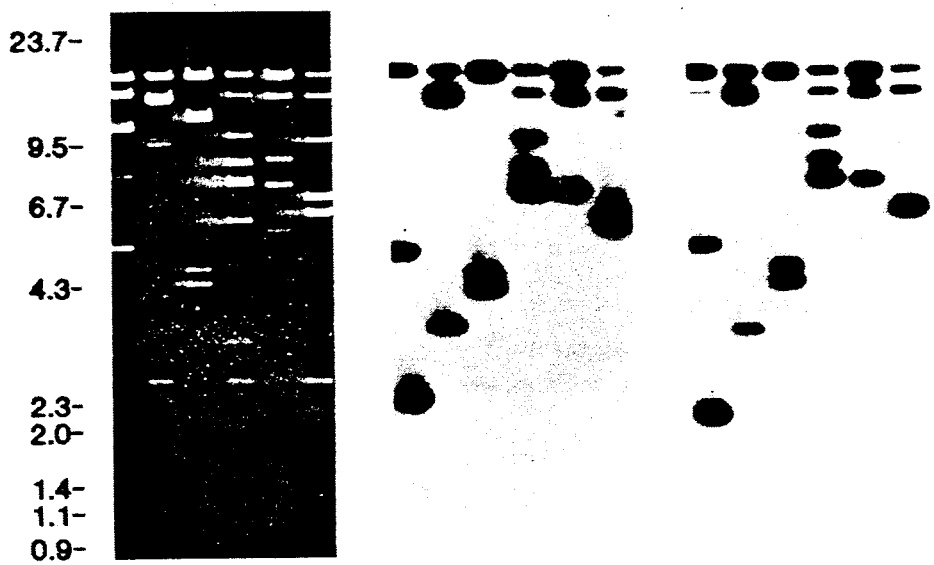
FIG.4B  B H X Sl S Xb
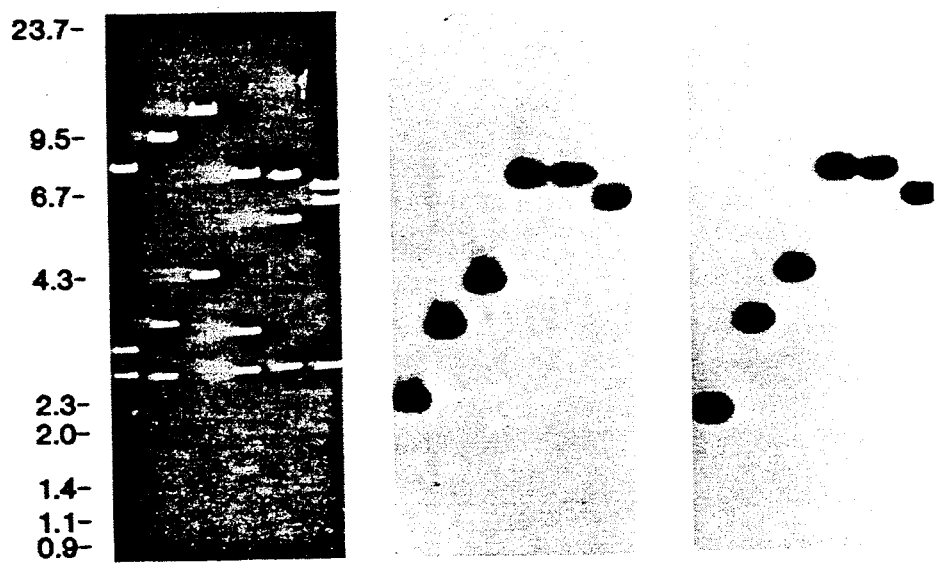
FIG.4C
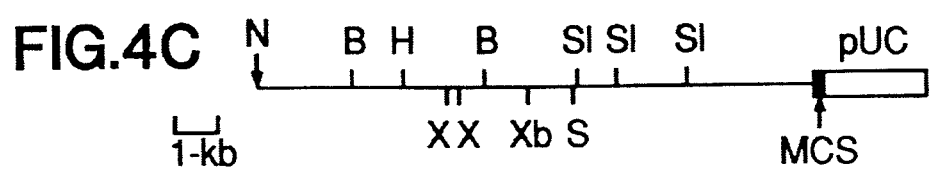

MODIFIED CLONING VECTORS FOR RESTRICTION MAPPING, THEIR PREPARATION AND USE

FIELD OF THE INVENTION

The invention relates to the field of molecular biology, and more particularly to modified cloning vectors which are of general utility for easily obtaining unambiguous restriction maps of recombinant deoxyribonucleic acid (DNA) molecules.

BACKGROUND AND PRIOR ART

Advances in the field of molecular biology over the last decade have made possible the identification and detailed study of genetically significant regions of specific DNA molecules. A necessary prerequisite to determining the positions of biologically important DNA regions of a given genome was the development of reliable restriction enzyme cleavage mapping techniques. A restriction map defines the sites on specific DNA molecule at which the DNA is cleaved by one or more restriction enzymes. Once a restriction map has been determined for a specific DNA molecule from a particular genome, the resulting map has reference value in any future experimentation involving the same molecule. In addition to providing much useful information about the organization of various DNA molecules, such mapping techniques were also instrumental in the development of DNA sequencing and recombinant DNA techniques.

A number of techniques are currently in use for obtaining DNA restriction maps. The mapping techniques most commonly used generally entail determination of the cleavage fragments in a complete restriction enzyme digest, followed by the tedious ordering of such fragments by various methods, typically involving analysis of a subset of fragments present in each of several overlapping partial enzyme digests. Usually such procedures are time consuming, and may produce less than satisfactory results if a restriction map of high resolution is desired.

One commonly used procedure for obtaining a restriction map is by digesting the DNA molecule of interest, or target DNA, with combinations of restriction enzymes. In order to simplify the procedure, a primary digestion is preferably carried out to limit the number of fragments produced. The primary digest is produced using an enzyme having an infrequent recognition sequence, such as enzymes that recognize hexanucleotide sequences. As is known, the primary DNA fragments may be isolated and recovered following separation, e.g. by electrophoresis. A DNA fragment obtained in the primary digest may be cleaved with additional restriction enzymes, and compared on a gel with appropriate markers of known size. From the data obtained, it is possible to postulate a restriction map which accounts for the observed array of fragments. In building up a restriction map by this procedure, one attempts to assign cleavage sites by trial and error to a uniquely ordered set of locations that are internally consistent with one another.

Resolution of the restriction map obtained by the above-described method of digesting a DNA sequence with a succession of restriction enzymes may be enhanced if the digestion is carried out with different restriction enzymes, both singly and together. By producing fragments from both single and double digestions, a greater array of fragments is generated for use in formulating a restriction map. Similarly, additional specificity concerning the restriction sites in a DNA molecule may be obtained by performing both complete and partial digestions with one or more restriction enzymes.

A variety of computational methods have been developed in an effort to increase the speed and accuracy of the above-described trial and error procedures. One such method uses a computer to calculate the most probable order of restriction sites from single and multiple restriction enzyme digests, Pearson, *Nucl. Acids Res.*, 10: 217-27 (1982). Another algorithm capable of ordering restriction fragments, but requiring only pencil and paper, has also been reported Fitch et al., *Gene*, 22: 19-29 (1983). Although these approaches are theoretically useful, in practice their application is limited by the requirement for extremely precise length measurements of every fragment in the digest. A missing fragment, even a very small one, or slight inaccuracies in measurement of fragment lengths can produce an erroneous map. In addition, such methods cannot unambiguously order a series of contiguous fragments terminated by the same restriction site.

In preparing a DNA fragment for purposes of restriction mapping, it has been proposed to work from a fixed point on the DNA sequence, for example, from one of the termini of the linear DNA sequence. One such end-labeling method has been reported by Smith and Birnsteil, *Nucl. Acids Res.*, 3: 2387 (1976). According to this method, a DNA fragment is first uniquely labeled at one end of the molecule. The end-labeled fragments are partially digested with a given restriction enzyme. By adjusting the conditions of digestion so that, on the average, only one cleavage occurs per molecule, a ladder of discrete, labeled DNA fragments is generated. The sizes of the resultant fragments reflect the distance between the labeled end of the DNA fragment and a given restriction site. The difference in size between two adjacent fragments on the gel defines the distance between neighboring restriction sites. Although this method yields an accurate restriction map, its general utility is limited, because in order to uniquely end label the DNA fragments, some prior knowledge of the restriction map is necessary as is the favorable placement of restriction sites.

The mapping technique utilizing end-labeling has been adapted for use in connection with cosmid-type vectors. According to this method, the left or right end of a linear phosmid vector (a cosmid vector derived from the phage μorigin of replication) is end-labeled by hybridizing to the vector a labeled oligonulceotide complementary to one end, followed by partial restriction enzyme digestion. This method, however, lacks versatility in that the preparation of phosmid DNA is time comsuming. The method is further limited in its application to cosmid-type vectors.

In view of the currently available procedures for DNA restriction mapping, it would be desirable to provide an improved method which is generally applicable for obtaining unambiguous, high resolution restriction maps of DNA molecules.

SUMMARY OF THE INVENTION

In order to avoid the limitations and difficulties experienced with existing restriction mapping techniques, various cloning vectors have been modified so as to be of general use for easily and unambiguously determining restriction maps of DNA molecules. In one aspect of this invention, vectors are provided which are characterized by the inclusion of a DNA construct comprising a linear, synthetic oligonucleotide made up of an infrequent cutter segment and a linker segment.

Suitable vectors for use in the invention are selected from the group of plasmid, lambda phage and cosmid cloning vectors. The particular vector selected will depend primarily on the size of the DNA molecule to be mapped. The construct is adapted to be readily inserted into the cloning vector. To this end, the DNA construct is preferably synthesized so as to contain cohesive termini in order to facilitate insertion of the construct into the appropriate vector. The linker segment is preferably positioned in the vector adjacent to a multiple cloning site, into which is inserted the target DNA sequence to be mapped.

According to another aspect of the present invention, there is provided a method for efficiently and effectively obtaining unambiguous restriction maps of DNA molecules. In performing this method, the modified vector including the DNA sequence to be mapped is first completely digested with a site specific restriction endonuclease that recognizes the recognition sequence of the infrequent cutter segment of the vector. The resultant digest comprises linear pieces of DNA comprising the target DNA molecule, with at least one terminus of the DNA pieces including the cleaved residue of the infrequent cutter segment adjacent thereto. The DNA pieces obtained from this first digest are subjected to digestion with at least one other site specific restriction endonuclease to yield a second digest comprising fragments of the linear pieces of DNA, a fraction of the fragments including the terminus having the cleaved residue of the infrequent cutter segment with adjacent linker segment. In the course of performing the method of the invention, the aforeseaid terminus is labeled with a detectable label, and the fraction of fragments obtained in the second digest are ordered on the basis of a measurable physical property, such as molecular weight. The order of the fragments is then determined by means of the detectable label, after which the measurable physical property of said fragments is correlated to the distance of the specific restriction site of each such other restriction endonuclease along the DNA molecule being mapped, as measured from the labeled terminus.

In one variation of the method of the invention, based on the Southern blot technique, the fragments obtained in the second digest are separated, e.g. by gel electrophoresis, and transferred to a filter paper, such as nitrocellulose, using known techniques. Each fragment is then hybridized to a 32$_{P\text{-}labeled}$ probe which is complementary to the linker segment of the DNA construct, which, due to the initial digestion at the infrequent cutter segment, is present on one terminus of each fragment. An autoradiographic exposure prepared from these fragments displays an overlapping array of fragments that are ordered from the labeled terminus, revealing the location of restriction sites within the target DNA molecule.

In an alternative approach, referred to herein as the recession hybridization detection (RHD) technique, after the first digestion of the above-described method is completed, the resulting DNA pieces are reacted with an exonuclease enzyme to recess the 3' ends. Recession occurs at the end of the DNA pieces containing the infrequent cutter linker construct which, as a result of the first digestion, is present at only one end of each DNA piece. To the exposed single-stranded end of each fragment created by exonuclease action is hybridized a labeled, synthetic oligonucleotide complementary to the exposed single-stranded DNA sequence. The labeled fragments are then further digested with the second restriction enzyme, separated, e.g. by gel electrophoresis, and exposed to X-ray film. The resulting autoradiographic pattern displays an array of fragments which are ordered from the labeled terminus, from which the location of restriction sites within the DNA molecule of interest is determinable.

Either variation of the restriction mapping method of the invention yields an ordered array of fragments of increasing lengths corresponding directly to the distance that the restriction sites are located from the labeled terminus.

Other aspects of the present invention include the method of making the modified vectors, the method of transforming host cells with the vectors, as well as the transformed host cell thus obtained.

Each of the various aspects of this invention are set forth more fully in the detailed description of the invention provided below.

TGA = a terminatio.1 codon);

* * *

Figure 1A:
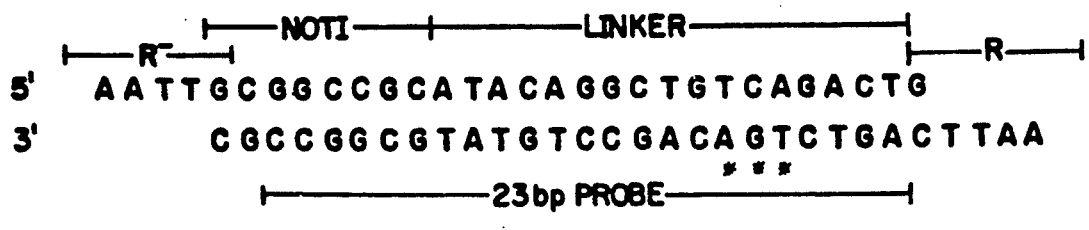
FIG. 1A represents a base pair sequence (RN-1) comprising a NotI/Linker construct for insertion into an EcoRI pUC multiple cloning site; the location of restriction sites and Linker region is indicated for this sequence (R = EcoRI; R$^-$ = defective EcoRI.
Figure 1B:
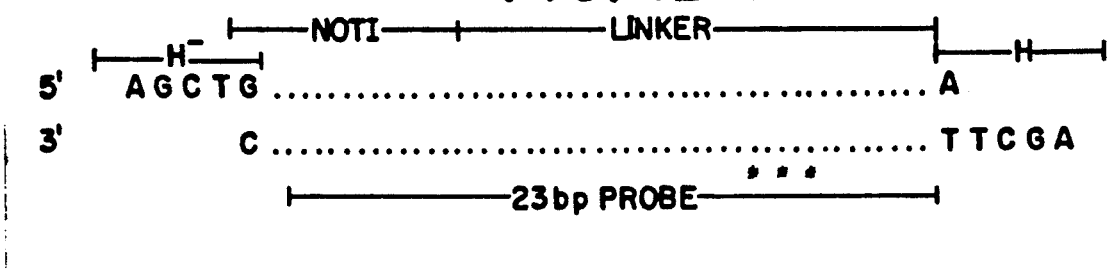
Figure 1C:
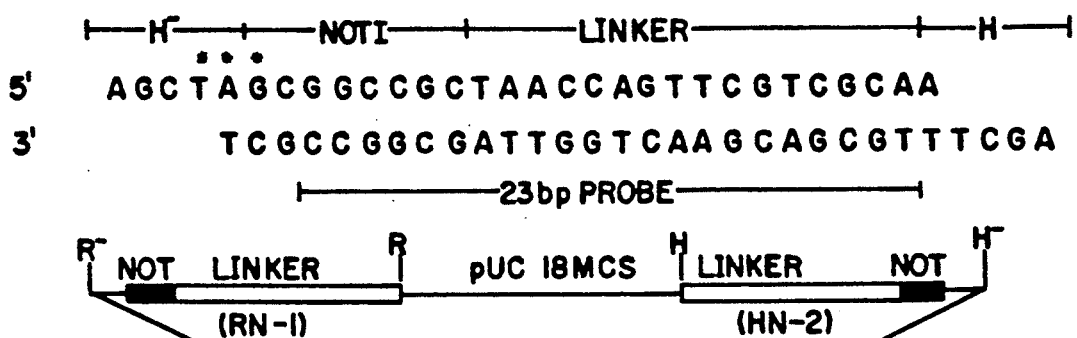
Figure 3:
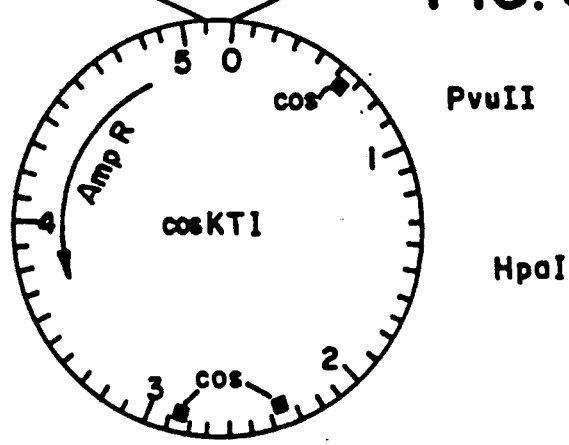
Figure 2A:
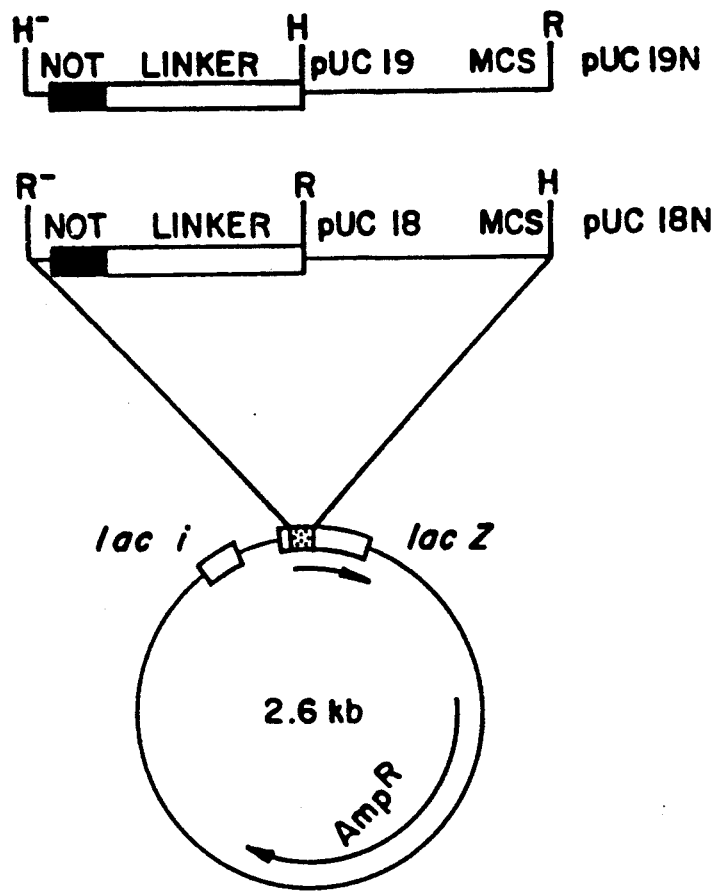
Figure 2B:
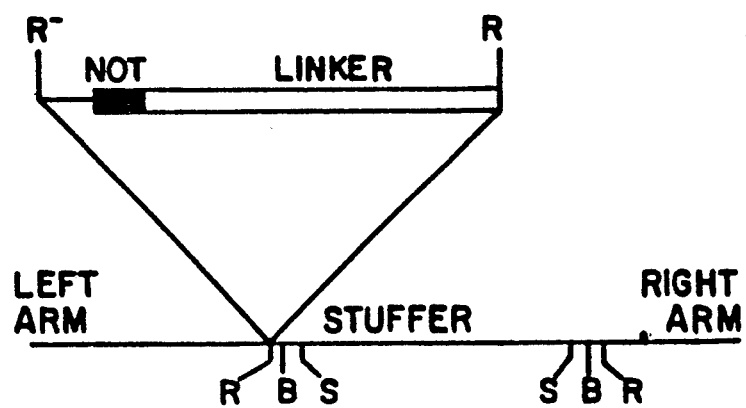

FIG. 1B represents a base pair sequence (HN-1) comprising a NotI/Linker construct for insertion into an Hind III pUC multiple cloning site; the NotI and Linker segments are as shown in FIG. 1A (as represented by the dotted lines); the location of restriction sites and linker region is indicated for this sequence (H=HindIII; H$^-$=defective Hind III);

FIG. 1C represents a base pair sequence of an oligonucleotide (HN−2) comprising a NotI/Linker construct having a Linker segment different from that shown in FIGS. 1A and 1B for insertion into a Hind III pUC multiple cloning sites; the location of restriction sites and Linker region is indicated for this sequence (H and H$^-$are as defined above); termination codon (TAG) is again denoted by astricks (***);

In FIGS. 1A, 1B and 1C, the 23 base pair oligonucleotide corresponding to the lower strand represents a DNA probe;

FIG. 2A illustrates a vector constructed in accordance with the invention derived from the plasmid pUC18 or pUC19 and including a NotI/Linker construct, with the location of its insertion shown adjoining the multiple cloning site (MCS) of the vector (R, R$^-$, H and H$^-$are as defined above);

FIG. 2B depicts a vector constructed in accordance with the invention derived from lambda phage strain EMBL4 and including a NotI/Linker construct with the location of its insertion shown at the EcoRI site on the left arm of EMBL4; the "Stuffer" segment represents a DNA fragment which functions in packaging the phage DNA; (R=EcoRI; B=Bam HI; and S=Sal I);

FIG. 3 depicts a vector constructed in accordance with the invention derived from the cosmid vector cosKT1, showing the insertion of two different NotI/-Linker constructs, with the linker segment of each oriented adjacent to the multiple cloning site of the cosmid vector cosKT1; this 5.2 kb cosmid contains three cos sites and unique Pvu II and HpaI sites, as indicated; (R, R−, H and H−are as defined above);

FIG. 4 illustrates the restriction mapping method of the invention according to the recession hydridization detection (RHD) and Southern blot procedures, using a plasmid vector of the type shown in FIG. 2A. including a DNA fragment containing the white gene of Drosophila. FIGS. 4A and 4B show the results of autoradiographic analysis of fragments obtained after digestion of the plasmid vector with NotI restriction enzyme, followed by partial digestion, (FIG. 4A) and complete digestion (FIG. 4B) with the restriction enzymes BamHI (B), HindIII (H), XhoI (X), SalI (Sl), SacI (S), and XbaI (Xb), corresponding to the lanes of the gel reading left to right; in FIGS. 4A and 4B the left hand panels were obtained by ethidium bromide staining of the DNA fragments present in the gel; the middle panels were obtained by Southern blot performed on the same gel using $^{32}$P-labeled probe complementary to the NotI/Linker construct (N); and the right hand panels were obtained using the RHD procedure; the size, in kilobases, of Hind III lambda and Hae III $\phi$174 molecular weight standards are shown at the left. FIG. 4C is a restriction map of the inserted DNA fragment, based on data from FIGS. 4A and 4B, with the location of the NotI/Linker construct, multiple cloning site (MCS) and pUC vector indicated.

Figure 5A:
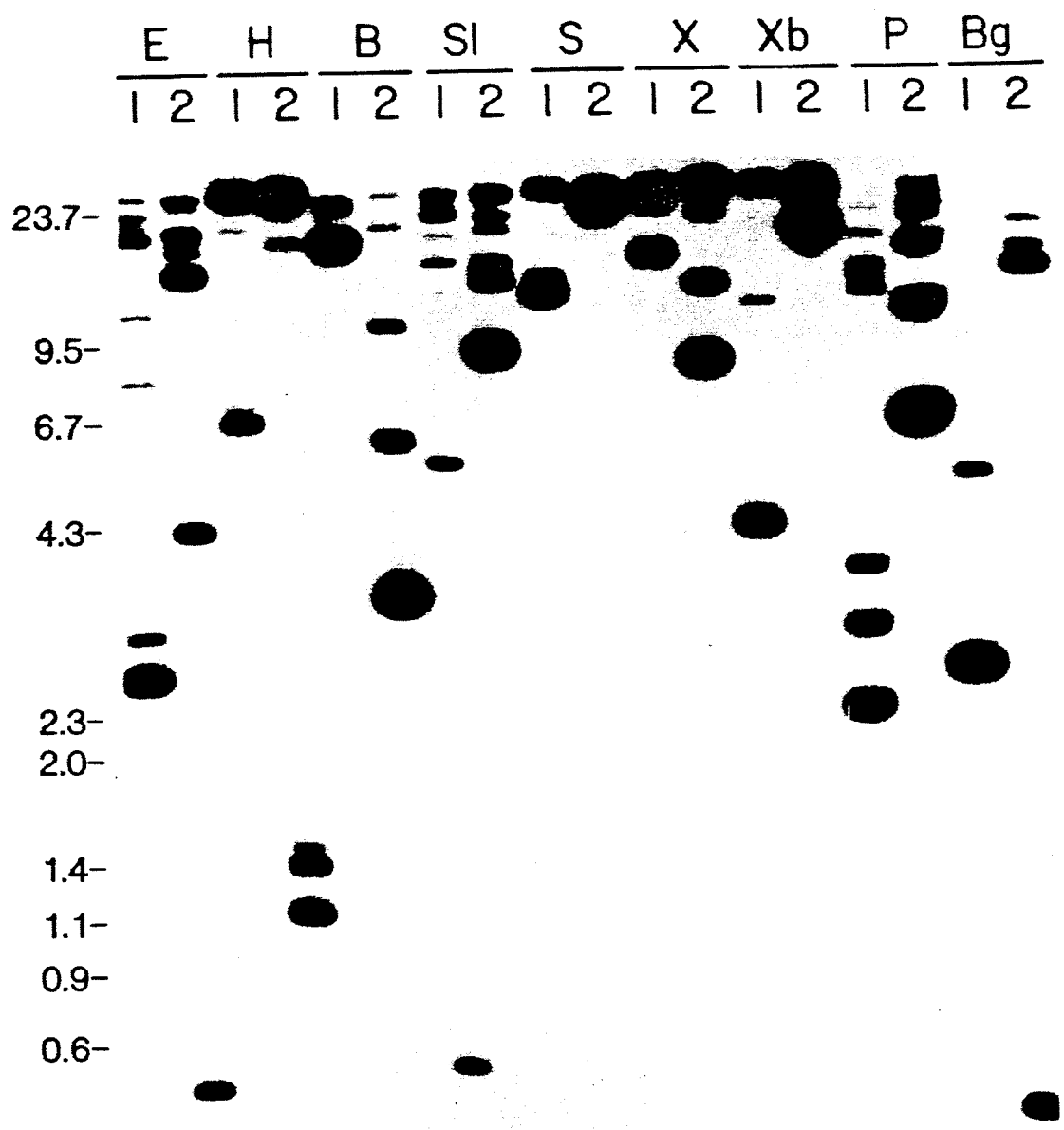

FIG. 5 illustrates the restriction mapping method of the invention according to the RHD procedure employing the cosKT1 cosmid vector (as shown in FIG. 3), including an insert greater than 30kb in length in the multiple cloning site. FIG. 5A shows the results of autoradiographic analysis of fragments obtained after digestion of the cosmid vector with NotI followed by recession of the 3' ends with exonuclease III, labeling with two different probes complementary to the two different NotI/Linker constructs used in preparing the vector, and subsequent partial digestion with the restriction enzymes EcoRI (E), BamHI (B), SalI (Sl), SacI (S), XhoI (X), XbaI (Xb), PstI (P), and BgII (Bg). The lanes are labeled 1 and 2 to indicate that samples in each lane have been labeled with the two different probes, respectively. Molecular weight standards (in kilobases) are shown at the left.

Figure 5B:
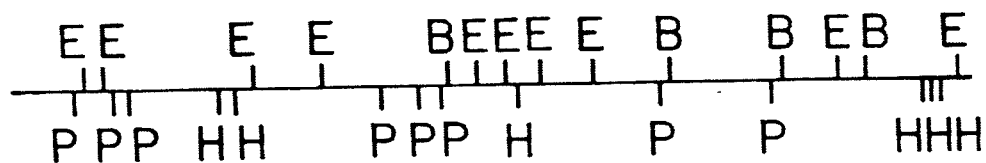

FIG. 5B is a restriction map based on the data from FIG. 5A. The map is constructed from left to right by reading the size of bands in the ladder of lane 1 from top to bottom. Similarly, the right to left end of the map is arrived at by reading the size of bands in lane 2 from bottom to top.

DETAILED DESCRIPTION OF THE INVENTION

The infrequent cutter segment of the DNA construct is so called because it is synthesized so as to contain a recognition sequence for a site specific restriction enzyme which would be expected to occur only once in about 65kb in a genome that is 50% GC. The recognition sequence of the infrequent cutter segment may be six (6) or more base pairs in length, and preferrably is at least eight (8) base pairs in length. Representative examples of infrequent cutter segments that may be used in the practice of this invention include GCGGCCGC, and GGCCNNNNNGGCC (N represents any nucleotide), which are recognized by the restriction endonucleases NotI and SfiI, respectively. Although various infrequent cutter segments may be used in practicing this invention, the invention will be described hereinafter with reference to the NotI restriction site, which is the preferred infrequent cutter segment for use in the present invention.

The DNA construct is preferably synthesized so that the infrequent cutter segment is adjacent to an appropriate linker segments. The length of the Linker segment may be varied between about 10bp to about 1000bp. The linker segment itself may have no specific function other than to serve as the target for the oligonucleotide probe normally used in the labeling step of the method. On the other hand, the linker segment may also be a transcription promotor, e.g. by substituting SP6 and T7 promoters in the DNA construct that can at once provide a target for the probe and effect transcription or expression of the target DNA either in vitro or in vivo.

The DNA molecule to be mapped, sometimes referred to herein as the target DNA, may be a double-stranded DNA from any source. Generally, the size of the target DNA may range in length, measured in terms of kilobases, from about 0.5kb to about 45kb. As previously noted, the length of the DNA sequence to be mapped will generally determine the type of cloning vehicle or vector employed in practicing the invention. As is known, plasmid and bacteriophage vectors may be used effectively to clone DNA fragments of up to about 20kb in length; and cosmid vectors may be used to clone DNA fragments of up to about 45kb in length.

The construct is adapted to be readily inserted into the cloning vector. To this end, the NotI/linker construct is preferably constructed to contain cohesive termini in order to facilitate insertion of the construct into the appropriate vector.

In a particularly preferred method of practicing the restriction mapping method of the invention, the rarely found NotI recognition site is inserted in the appropriate cloning vector adjacent to a synthetic linker sequence that, in turn, is followed by a multiple cloning site. The construction of a vector containing a multiple cloning site may be carried out according to the procedure of Perron et al., *Gene*, 33: 103-19 (1985). The NotI/Linker construct provides a unique site for cutting the vector at the construct and for labeling the NotI cut end attached to the target DNA in the multiple cloning site. In other words, when vectors containing the NotI/linker construct are cloned with target DNA and the vectors completely digested with NotI, each resulting fragment has a unique terminus comprising the residue of the NotI restriction site adjacent to the linker.

The description which follows sets forth the general procedures involved in practicing the present invention. All temperature are given in degrees Centigrade, unless otherwise indicated. To the extent that specific materials are mentioned, it is merely for purposes of illustration and is not intended to limit the invention.

a. Vector Systems and Appropriate

Hosts Therefor

It has been discovered that different cloning vectors may be employed in practicing the present invention.

Indeed, most of the more commonly-used vectors have been successfully applied in constructing restriction maps according to this invention. Suitable vectors include the pUC plasmid vectors, such as pUC18 or pUC19, which both possess the lacZ complementation system. These vectors are used to particular advantage in that colonies of bacteria successfully transformed therewith are readily identifiable using known techniques.

The plasmids pUC18 and pUC19, described in Perron et al., *supra* 33:103 (1985), may be routinely propagated in *E. coli* strain DH5λ, available from Bethesda Research Laboratories. The pUC plasmids, as well as their derivatives described hereinafter, are grown in LB medium or "T-broth" (TB) medium. Preparation of LB medium is described in Maniatis et al., *Molecular Cloning*, Cold Spring Harbor Laboratory (1982) (hereinafter "Maniatis"). One liter of TB is made by adding 100 ml. of a sterile solution of 0.17 M $KH_2PO_4$ and 0.72 M $K_2HPO_4$ to a separately sterilized solution containing 12g. bacto-trYptone, 24 g. bacto-yeast extract, 4.0 ml. glycerol, and water to a final volume of 900 ml.

Liquid cultures of lambda phage EMBL4, as described in Frisçhauf et al., *J.Mol.Biol.*, 170: 827(1983), and related phage, are grown on *E. coli* stain BHB2600 in NZYM medium, as disclosed in Maniatis, supra. Phage stocks, and phage derived by *in vitro* packaging, were titered or amplified using *E. coli* strain LE392, and plated on soft agar in the customary manner.

A preferred cosmid vector is cos4, constructed as disclosed in Steller et al., *EMBO J.*, 4:167(1985). The cos4 vector, and its derivatives, were propagated in *E. coli* strain DH1 or DH5α and cultured in TB medium. Xgal and ampicillin were added to agar plates or broth as necessary. It is noted that when DH1 or DH5 α are grown in LB broth, a typical yield of cosmid DNA is about 100μ g. per 330 ml. of culture. With the use of TB medium, however, it was found that about 2 mg. of cosmid DNA per 330 ml. of culture can be routinely obtained. Therefore, by growing bacteria in TB medium, it is possible to process many 50 to 100 ml. cultures, and to obtain approximately 250μ g. of cosmid DNA. TB has also been found to increase the yield of pUC plasmids.

b. Preparation of DNA Construct

The synthetic oligonucleotides including the NotI/-linker construct may be prepared by the phosphoramidite method employing the Applied Biosystems 380A DNA synthesizer or similar devices. The resultant construct may be purified according to procedures well known in the art, e.g. by electrophoresis on a 10% polyacrylamide gel.

c. Target DNA Preparation.

In order to prepare target DNA, plasmid-bearing bacteria are grown to saturation overnight with vigorous shaking at 37°. Plasmid DNA is readily obtained by the alkaline lysis procedure described in Maniatis, supra. It has been found preferable to carry out an additional phenol extraction step after precipitation of the DNA from the CsCl gradient. The additional extraction step eliminates trace amounts of exonuclease that frequently contaminate plasmid DNA preparations. The presence of such contaminants can result in a slightly smeared appearance to the bands produced after restriction enzyme digestion.

Quantities of lambda phage are prepared by adding $1.3 \times 10^8$ phage to 6.7 ml. of a saturated culture of *E. coli* strain BHB2600 grown in NZY medium and incubating at 37° for 20 minutes. The infected culture is then transferred to 330ml of NZYM broth in a 2 liter flask and vigorously shaken at 37° for about 6 hours, at which time complete lysis is apparent. The lysate is adjusted to 0.5 M NaCl and 0.02 M $MgCl_2$ and cell debris is removed by centrifugation, and the phage precipitated with polyethylene glycol(PEG 8000). Lambda DNA is extracted by the method of Thomas et al., *J. Mol. Biol.*, 91: 315 (1975).

Drosophila DNA was prepared as described in Tartof et. al., Cell, 37: 869 (1984).

d. Vector Preparation.

Plasmid or lambda DNA is digested at 37° for 60 minutes with a 4-fold excess of restriction enzyme in 20 to 50μl. of universal restriction buffer (URB), comprising 33 mM Tris acetate, pH 7.9; 66 mM potassium acetate; 10 mM magnesium acetate; 100 μg./ml. BSA; 0.5 mM dithiothreitol; and 4 mM spermidine. All of the restriction enzymes tested possess the same activity in URB buffer as in the manufacturer's recommended buffer. To insert the NotI/Linker construct into a vector of choice, 5 μ g of the complementary strands of the appropriate unphosphorylated synthetic oligonucleotide are annealed in 10 μl of ligase buffer (20 mM Tris acetate, pH 7.4; 7.5 mM $MgCl_2$; 0.1 mM EDTA; 0.5 mM ATP; and 1.0 mM DTT) at 37° for 60 minutes to produce the desired double-stranded segments. One microgram of this DNA is ligated to an equal amount of restriction emzyme-digested plasmid or lambda DNA in 10 ml. of ligase buffer containing 3 units of T4 ligase and 50 μg./ml. BSA, and incubated at 16° for 12 to 24 hours. Cells competent for transformation by plasmid DNA were prepared as described in Maniatis, supra, and plated on LB-agar plates supplemented with ampicillin and/or Xgal as necessary. Ligated lambda DNA is packaged into phage and plated on *E. coli* stain LE392 in the usual manner.

e. Insertion of Target DNA into vectors

Recombinant DNA libraries may be prepared with the plasmid vectors pUC18 and pUC19 containing the NotI/linker construct by digesting both vector and target DNA with the restriction enzyme of choice, ligating with T4 ligase, and transforming DH5 λ host cells. Each of these recombination steps may be performed according to standard procedures disclosed in Maniatis, *supra*.

Genomic libraries are generated with the NotI/linker construct inserted in lambda vector EMBL4 as in the following manner. The genomic DNA of choice is first partially digested with MboI, then treated with calf intestinal alkaline phosphatase followed by two phenol extractions, ethanol precipitation, and redissolved in TE buffer (10 mM Tris acetate, pH 7.4; 1 mM EDTA). One microgram of DNA was combined with 0.5 μg of recombinant EMBL4 previously digested to completion with the enzymes BamHI and SalI, and the mixture was ligated with T4 ligase. The products of this reaction were packaged *in vitro* into lambda phage and propagated in *E. coli* strain LE392 by plating on soft agar. Using Drosophila DNA, it is normal to obtain about $2 \times 10^6$ plaques per microgram of target DNA.

Cosmid libraries are prepared by ligating 2.5ug of MboI partially digested and dephosphorylated genomic DNA to 2.5ug of cosmid vector digested with BamHI and HpaI. The ligated DNA is packaged in vitro and 50ul of the resulting phage is used to infect 100 1 of a freshly saturated culture of *E. coli* strain DH1 or DH5 λ grown in NZYM medium. After incubating bacteria and phage at 37° for 30 minutes the cells are spread on ampicillin plates. Cosmid libraries prepared from Drosophila DNA in this manner yield approximately $1 \times 10^5$ colonies per microgram of genomic DNA.

f. Preparation of Labeled DNA Probe

A synthetic oligonucleotide complementary to the NotI/linker construct is conveniently prepared by the phosphoramidite method described in section (b) above. 200 ng. of this oligonucleotide is added to a 30 μl reaction mixture containing kinase buffer (70 mM Tris acetate, pH 7.6; 10 mM $MgCl_2$; 5 mM dithiothreitol), 12 units polynucleotide kinase, 18 μl $^{32}$P-ATP (4500Ci/mM) and incubated for 90 to 120 minutes at 37° C. The reaction is terminated by the addition of 6 μl of 0.25M EDTA followed by heating at 70° for 5 minutes. The labeled oligonucleotide is separated from unincorporated label by adding sodium acetate (pH7.4) to a final concentration of 0.7M, 20 ug/ml tRNA and 2 volumes of isopropanol. The resulting precipitate is washed with 95% ethanol, dried, and resuspended in TE buffer.

In addition to the radioisotope-labeled oligonucleotide probes which have been successfully employed in practicing the present invention, similar results should be obtainable using non-radioactive labels. End-labeling of the appropriate oligonucleotide may be accomplished using biotin (the latter having a known affinity to avidin, which has been widely utilized in labeling DNA fragments) or a fluorochrome, for example.

g. Determination of Restriction Maps Using Vectors Containing the NotI/Linker Construct Constructing a restriction map of target DNA in accordance with the invention is accomplished by using one of the two methods briefly mentioned above for labeling and identifying the enzyme digested fragments. The first method makes use of the Southern blotting technique, whereby the fragments are transferred after separation on a gel to a suitable filter. The fragments are thereafter hybridized, on the filter, to a DNA probe complementary to the NotI/linker construct, prepared as described above. It is also possible to map a number of different enzyme-generated fragments on a single gel, for visualization and comparison.

The particular protocol described below, which is provided in order to illustrate and not to limit the scope of the invention, is designed to map up to 10 different restriction enzyme recognition sites on a target DNA molecule inserted into any one of the vectors herein described.

(i) Restriction Mapping by the Southern Blot Procedure

Initially, 20 μg of DNA is completely digested with 100 units of NotI restriction enzyme in 200 μl of URB for 60 minutes at 37°. The digested DNA is adjusted to 100 mM Na acetate and precipitated with two volumes of ethanol. The precipitate is washed once with 70% ethanol, dried and then redissolved in 10 mM Tris acetate (pH 7.4) at a concentration of 0.4 μg DNA/μl. For each restriction enzyme to be mapped, 5 μl (2 μg) of Not I digested DNA are added to a tube containing 5 μl of 10×URB and a sufficient volume of water to bring the final volume to 50 μl after restriction enzyme is added. The tube is equilibrated in a water bath at 25° and then 6-10 units (usually 0.5-1.0 μl) of restriction enzyme are added. After 1 minute, 12.5 μl are removed and added to a tube containing 3 μl of stop solution (100 mM EDTA, 6.0 M urea, 25% sucrose and 0.5% Orange-G). The remaining reaction is then transferred to a water bath at 37° After one minute another 12.5 μl are removed and combined with the previously terminated 25° partial digest reaction. This tube now contains a representative assortment of partial digests spanning about a four-fold range of partial digestion. An additional 1 μl of the appropriate restriction enzyme is added to the remaining 25 μl and incubation continued at 37° for 60 minutes to produce a complete digest. This reaction is terminated by the addition of 3 μl of stop solution.

It will be clear to those skilled in the art that the specific reaction volumes given, as well as the DNA and restriction enzyme concentrations described, can be adjusted to achieve optimum results for virtually any restriction enzyme or vector combination.

The partial and complete digests prepared for each restriction enzyme undergo electrophroresis on a 0.6% agarose gel and the resulting DNA fragments are transferred from the gel to a suitable membrane filter (for example, the Dupont Genescreen Plus) by capillary action. The filters, which are usually 20×20 cm. in size, are incubated in 30 ml. of a solution containing 10% dextran sulfate, 1.0 M NaCl, 1% SDS and 25 mM phosphate buffer (pH 7.0) at 68° for 4 hours. Thereafter, $3 \times 10^6$ cpm of $^{32}$P-labeled DNA probe was added and the incubation continued for another 16 to 24 hours at 55°. Following hybridization the filter is rinsed in 0.1% SDS, twice in 1 mM Tris HCl (pH 7.5) for 20 minutes at room temperature, dried, and exposed to X-raY film at −70° using an intensifying screen.

(ii) Restriction Mapping by the Recession Hybridization Detection Procedure As an alternative to the above-described technique, the fragments may be labeled and identified by recessing the 3' ends of the fragments using an exonuclease and hybridizing the fragment with a complementary probe. In a protocol illustrating this embodiment, 20 ug of cloned DNA constructed to contain the NotI/linker construct is digested with NotI restriction enzyme in a volume of 300 μl. and incubated at 37° for 60 minutes. Six units of exonuclease III, appropriately diluted in storage buffer (200 mM KCl; 0.05 M EDTA; 5 mM potassium phosphate, pH 6.5; 5 mM B-mercaptoethanol; 200 μg./ml. BSA; 50% glycerol), is added to the reaction mixture and incubated at 37° for an additional 10 seconds, after which time both enzymes are inactivated by heating at 70° for 5 minutes. Approximately $2 \times 10^6$ cpm of $^{32}$P-labeled NotI probe, with a base sequence complementary to the single-stranded 5' ends exposed as a result of exonuclease digestion, are added and allowed to hybridize with the 5' ends of the fragments at 37° for 60 minutes. The reaction is adjusted to 100 mM sodium acetate and the DNA precipitated by the addition of ethanol, washed with 70% ethanol, dried and redissolved in 10 mM Tris acetate (pH 7.4). Partial and complete restriction enzyme digestions are then carried out in the manner described above. Following electrophoresis, the gel is transferred to chromatography paper (3MM Whatman), and the exposed gel surface is covered with a plastic wrap and placed in a gel dryer. By partially drying the gel under a vacuum, without heat, the gel is reduced to a thin film after about 30 minutes, and exposed to X-ray film as described above.

The following examples are provided to describe the invention in further detail. These examples, which set forth the best mode presently contemplated for carrying out the invention, are intended to illustrate and not to limit the invention. Here again, all temperatures are given in degrees Centigrade, unless otherwise indicated.

EXAMPLE 1

Preparation of NotI/Linker Constructs and Probes

Three separate NotI/Linker constructs, each 30 base pairs in length, were synthesized by the phosphoramidite methanol. The resultant constructs are represented in FIGS. 1A, 1B, and 1C of the drawing. As previously noted, it is useful to construct each terminus of the NotI/Linker construct with a ligatable cohesive end portion, to simplify inserting the construct into the various vectors. The NotI/Linker construct depicted in FIG. 1A was synthesized such that the left-end terminus contains a ligatable, but not subsequently digestible, defective EcoRI site (RI−), followed by the 8-base pair NotI recognition site, followed by a 17-base pair Linker segment. The 17-base pair Linker segment is in turn terminated by a cohesive EcoRI site (RI+) which, when ligated, can be subsequently cut with EcoRI. The NotI/Linker construct of FIG. 1A (designed "RN-1") was designed such that when inserted in the desired orientation into the multiple cloning site of the lacZ gene of various vectors, it will be in the proper reading frame to permit full lacZ function. However, if inserted in the opposite orientation, the termination codon

TGA,
. . .

will be read, thereby preventing formation of a functional lacZ product.

Other variations of the same NotI/Linker construct may be prepared for vector insertion. The NotI/Linker construct shown in FIG. 1B, for example, contains the identical 17-base pair Linker segment as that shown in FIG. 1A, in addition to the 8-base pair NotI recognition site. The sequence shown in FIG. 1B (designated "HN−1") is constructed with one HindIII−(defective HindIII) cohesive terminus and one HindIII cohesive terminus. As in the previously-described sequence, the reading frame is positioned to maintain lacZ function when the sequence is inserted.

FIG. 1C shows an alternate construct (designated "HN−2") containing HindIII and HindIII−cohesive termini, but with a distinctly different Linker segment.

The synthetic 23bp oligonucleotides (FIGS. 1A, 1B and 1C), corresponding to the lower strand of each duplex, will serve, when end-labeled with $^{32}P$, as probes for the linker segment. The orientation of the RI/NotI and HindIII/NotI sequences can be confirmed following insertion into the appropriate vector by mapping with the appropriate restriction enzymes and DNA sequencing, as disclosed in Sanger et al., *J. Mol. Biol.*, 143: 161 (1980).

EXAMPLE 2

Insertion of the NotI/Linker

Construct into pUC Vectors

The RN-1 and HN-1 constructs prepared as described in Example 1 were inserted at the RI and HindIII sites of pUC19 and pUC18 to form pUC19N and pUC18N, respectively, as illustrated in FIG. 2A. As seen in FIG. 2A, the construct is inserted adjacent to the multiple cloning site of the pUC plasmids. It is noted that since pUC19N and pUC18N have the lacZ gene function preserved, in the appropriate host cells, for example DH5, they give rise to blue-colored colonies when grown on Xgal agar plates. When target DNA is inserted into the multiple cloning site of these vectors, white-colored colonies are produced. Transformation was accomplished by standard procedures, disclosed in Maniatis, *supra*.

EXAMPLE 3

Insertion of the NotI/Linker Construct into the EMBL4 Lambda Vector

The RN-1 construct described in Example 1 above was inserted into the RI site on the left arm of EMBL4 as depicted in FIG. 2B. The resulting chromosome is referred to as EMBL4N, and has a cloning capability of 9-23kilobases. The orientation of the "stuffer" fragment in the EMBL4N is identical to that in EMBL4. See Frischauf et al., *J. Mol. Biol.*, 170: 827 (1983).

EXAMPLE 4

Construction of a NotI/Linker

Containing Cosmid Vector

The recombinant cosmid vectors shown in FIG. 3 was constructed using the cos4 cosmid vector, a cosmid vector previously employed by Steller et al., EMBO J., 4: 167 (1985). The cos4 vector was first digested with BamHI and AvaI, and the resulting 1.kb Bam-Ava fragment was removed and the remaining staggered ends ligated together after being repaired with DNA polymerise. The RN−1 and HN−2 linkers described in Example 1 were then inserted into the EcoRI and HindIII sites, respectively, in the orientations indicated in FIG. 3. In addition, the small fragment between the EcoRI and HindIII sites was replaced with the multiple cloning site from pUC18. The resulting vector, designated cosKT1, is 5.2kb in size and has a maximum cloning capability of approximately 45 kilobases.

It will be appreciated that because the in vitro assembly of cosmid DNA in mature phage results in the packaging and subsequent infection of a virus size genome terminated by cos sites, the cosmid clones ultimately obtained contain only 3.1 kb of the original vector spanning the distance between the two cos sites from 2.8 kb and proceeding in a clockwise direction to 0.7 kb. Vector sequences (proceeding clockwise) between 0.7 and 2.8 kb are deleted as a result of the packaging process.

Since standard electrophoretic conditions do not resolve fragments greater then 23kb, partial digests of the cosmid clones containing larger sequences cannot be entirely mapped from one labeled end terminus alone. For this reason, the cosmid vector cosKT1 possesses two NotI/Linker constructs that flank the inserted target DNA segments. When two DNA constructs are used in such cases, the Linker segment of each construct should be different, so that the fragments produced from each end following digestion with NotI and a second restriction enzyme will be distinguishable when the restriction map is obtained from the digested fragments. In this way, it is possible to determine restriction maps of such clones from either end.

EXAMPLE 5

Comparative Test Employing vector Containing the NotI/Linker Construct

To compare the restriction mapping method of the invention with the conventional trial and error method, a known DNA fragment was selected The selected fragment was a 12.8kb EcoRI fragment containing the white gene of Drosophila, the restriction map of which has been previously established. See Levis et al., Proc. Nat. Acad. Sci., 79: 564 (1982). This EcoRI fragment, which extends from −6.0kb to +6.8kb on the molecular map of the white gene, was cloned into pUC18N and restriction mapped with the aid of the NotI/Linker construct. Identification and labeling of the fragments was accomplished in separate trials using both the Southern blotting procedure and the RHD procedure. In the RHD procedure, a $^{32}$P-labeled lower strand from the NotI/Linker construct designated RN-1 (See FIG. 1A) was used as a probe. The pUC18N vector containing the 12.8kb fragment was first completely digested with NotI, followed by partial digestion in aliquots with the restriction enzymes BamHI, HindIII, XhoI, SalI, SacI, and XbaI. As disclosed in FIGS. 4A and 4B, the Southern blotting procedure and the RHD procedure yield virtually identical restriction patterns, and the map constructed from either set of data (FIG. 4C) is the same as that previously obtained by conventional methods.

Because the NotI/Linker insert sequence uniquely labeled only one of the cloned fragments, each labeled band in the partial digest corresponds to the distance that the restriction site lies from the NotI/Linker construct. The restriction map derived from these data (FIG. 4C) proceeds from left (the NotI/Linker end) to right by reading fragment lengths in each lane of the partial digests from bottom to top. In the autoradiographs of the partial digests the upper band, at 15.5 kb, in each lane corresponds to NotI-digested linear full length DNA. The band just below, at 13.8kb, indicates the presence of a restriction site in the multiple cloning site. No Xho site is present in the MCS and so a 13.8kb fragment is not present in the Xho partial digest lane. With the RHD procedure, autoradiogrphic exposures usually require only 1 to 4 hours. To insure that no rapidly cut sites are missed, it is useful to confirm maps constructed from partial digests with longer (overnight) exposures and/or the sizes of fragments observed in the corresponding complete digest.

It should also be noted in connection with FIG. 4A and 4B that the RHD technique produced a somewhat sharper banding pattern than was obtained using the Southern blotting method. This may result from the fact that when using the Southern blotting method there is considerable opportunity for diffusion of the DNA fragments during the transfer step from agarose to the membrane filter. Since the RHD technique eliminates the transfer step, diffusion may be reduced.

EXAMPLE 6

Restriction Maping a Cosmid Vector Using the RHD Technique

Under standard electrophoretic conditions it is difficult to resolve fragments greater than 23 kb in length, and accordingly, it is difficult to map cosmid-size inserts from only one labeled terminus. The cosmid vector coskT1 shown in FIG. 3 contains two distinct NotI/-Linker constructs.

In order to demonstrate the applicability of the invention to conmid-size inserts and the advantage of mapping such inserts from both ends, the present test was performed. The vector cosKT1 was prepared as described in Example 4 to contain the constructs designated RN−1 and HN−2, and the pUC18 multiple cloning site. A cosmid library was next obtained from a partial MboI digest of Drosophila DNA ligated to cosKT1 previously digested with BamHI and HpaI. A clone designated cDcs-2, which contained a 35 kb insert of Drosophila DNA, was selected from the library and its restriction map determined according to the following procedure. A sample of the cosmid clone was completely digested with NotI and reacted with exonuclease III, as described previously. The sample was then divided into halves. One half of the sample was annealed to a $^{32}$P-labeled probe corresponding to the lower strand of RN−1 (see FIG. 1A) and the other half-sample was annealed to a $^{32}$P-labeled probe corresponding to the lower strand of HN−2 (see FIG. 1C). Although a 23 bp probe is preferred for labeling purposes (and is reflected in FIG. 1C), a somewhat larger probe was utilized in performing the test on which FIG. 5 is based. It is believed that due to the presence of ligase activity, dimer formation occurred which produced a faint band on the gel. Substitution of the 23 bp probe seemed to eliminate this interference with the analysis. The RN−1 and HN−2 probes hybridize to the single-stranded 5' ends of the NotI/Linker constructs exposed by exonuclease digestion.

Each half-sample was divided into nine portions and partially digested with one of nine (9) different restriction enzymes (E=EcoRI; H=HindIII; B=BamHI; Sl=SalI; S=SacI; X=XhoI; Xb=XbaI; P= PstI; and Bg=BglII). Referring to FIG. 5A, the lanes labeled 1 and 2 for each enzyme contain samples that were annealed to RN−1 and HN−2 probes, respectively. Molecular weight standards (in kilobases) are shown at the left of FIG. 5A. A restriction map derived from the results is shown in FIG. 5B. For clarity, only four of the nine enzymes (E, P, H and B) are shown on the restriction map. The map is determined from left to right by reading the size of bands in the ladder of lane 1 from bottom to top. Similarly, the right to left end of the map is determinable by reading the size of bands in lane 2 from bottom to top. The accuracy of the map shown in FIG. 5B was confirmed by single and double digestions of DNA using the appropriate restriction enzymes. Libraries of target DNA may also be constructed using partial EcoRI, HindIII, or SmaI digestion in addition to the partial MboI treatment here described.

A potential limitation of the disclosed method and vectors is the occurrence of the NotI restriction site within the target DNA molecule itself, which would serve as a terminal boundary to which the insert may be prematurely mapped. Assuming a completely random distribution of the four nucleotides, the Poisson distribution predicts that the 8-base pair NotI recognition site would be expected to occur only once in about 65 kilobases. The Poisson distribution p(n), is defined as follows:

$$P(n) = \frac{r^n}{n!} e^{-r}$$

where $$r = \frac{\text{arbitrary fragment length}}{\text{average fragment length for a NotI site}}$$

and n = number of NotI sites.

In the case of Drosophila DNA, the Poisson distribution predicts that for 40kb fragments (r=40kb/65kb) 54% of the clones will have no (n=0) NotI sites, 34% one NotI site, and 12% two NotI sites. When nine Drosophila cosmid clones were chosen at random and digested with NotI, no NotI sites were found in 4 of the clones (45%), whereas 3 contained one site (33%) and 2 contained two sites (22%). From this sample it appears that the predicted and observed frequencies are in sufficiently close agreement to be consistent with the hypothesis that NotI sites are randomly distributed in the Drosophila genome. Thus, the present cosmid vectors are capable of completely mapping 88% of the inserts. Even when two or more NotI sites are present in the inserts, the terminal regions of the insert are still mappable.

For pUC18N, pUC19N and EMBL4N vectors the usual insert size is about 15kb. Here, a Poisson distribution predicts that 80%, 18% and 2% of such clones will have 0, 1 or 2 NotI sites, respectively. Since about 80% of Drosophila cosmids contain one or no NotI sites most inserts are entirely mappable by the method of the invention. These vectors are improved by incorporating two NotI/Linkers, each flanking the inserted DNA sequence so that a restriction map for virtually any plasmid or lambda clone (98%) may be constructed. The problem is reduced in the context of the mammalian genome due to the selection against the potentially methylateable sequence CpG. See, Swartz et al., J. Bio. Chem., 237: 1961 (1962). The NotI recognition sequence contains two such sequences. As a result, it has been estimated that the NotI sequence occurs only once in every 3000kb. See, Drmanac et al., Nuel. Acids Res., 11: 4691 (1986). The few NotI sites that do occur will most likely occur clustered in GC-rich regions (HTF islands) that show no suppression of the CpG sequence. See, Bird et al., Cell, 40:91 (1985); Brown et al., Nature, 322: 477 (1986).

While certain preferred embodiments of the present invention have been described and specifically exemplified above, it is not intended to limit the invention to such embodiments, but various modifications may be made thereto, without departing from the scope and spirit of the present invention, as set forth in the following claims. For example by selection of an appropriate label for the probe used in practicing the mapping method of the invention, this method may be adaptable to automated or semi-automated operation, in which restriction map data can be calculated either in real time during electrophoresis, or at the conclusion of electrophoresis to produce an unambiguous restriction map.

What is claimed is:

1. A modified cloning vector for facilitating mapping of a DNA molecule present in said modified cloning vector, said vector having a multiple cloning site including said DNA molecule and a DNA construct, said construct being a linear, synthetic oligonucleotide consisting essentially of an infrequent cutter segment providing a recognition sequence for a site-specific restriction enzyme, said recognition sequence being at lest eight base pairs in length, and a discrete, hybridizable linker segment, said construct being positioned in said vector with said linker segment adjacent to said DNA molecule.

2. A modified cloning vector as claimed in claim 1, wherein said recognition sequence is GCGGCCGC.

3. A modified cloning vector as claimed in claim 1, wherein said vector is selected from the group consisting of a plasmid, a lambda phage and a cosmid.

4. A modified cloning vector as claimed in claim 3, wherein said vector comprises two DNA constructs, said recognition sequence of each construct being the same and said linker segment of each construct being different with respect to nucleotide sequence, and wherein said multiple cloning site including the DNA molecule to be mapped is located intermediate the two DNA constructs, adjacent the linker terminus of each construct.

5. A modified cloning vector as claimed in claim 3, wherein comprises a plasmid selected from the group consisting of pUC 18 and pUC 19.

6. A modified cloning vector as claimed in claim 3, which comprises the lambda phage EMBL 4.

7. A modified cloning vector as claimed in claim 3, wherein comprises the cosmid cos4.

8. A modified cloning vector as claimed in claim 7, wherein said cos4 vector comprises two DNA constructs, each construct comprising a linear, synthetic oligonucleotide including an infrequent cutter segment and a linker segment, the infrequent cutter segment of each construct being the same and the linker segment of each construct being different with respect to nucleotide sequence and wherein the multiple cloning site of said vector is located intermediate said DNA constructs adjacent the linker terminus of each construct.

9. A vector as claimed in claim 8, wherein said multiple cloning site is a plasmid-derived oligonucleotide.

10. A method of preparing a modified cloning vector useful for obtaining a restriction map of a DNA molecule present in said vector, said method comprising inserting into a cloning vector a DNA construct, said construct being a linear, synthetic oligonucleotide consisting essentially of an infrequent cutter segment providing a recognition sequence for a site-specific restriction enzyme, said restriction sequence being at least eight base pairs in length, and a discrete, hybridizable linker segment, said construct being positioned in said vector with said linker segment adjacent to said DNA molecule and wherein said vector comprises a multiple cloning site including said DNA molecule and said DNA construct is positioned adjacent to said multiple cloning site.

11. A method as claimed in claim 10, wherein said construct is inserted into a vector selected from the group consisting of a plasmid, a lambda phage or a cosmid.

12. A host cell transformed in vitro with the vector of claim 1, and cells grown from said host cell, said cells containing said vector.

13. A DNA construct for facilitating restriction mapping of a DNA molecule, said construct being a linear, synthetic oligonucleotide consisting essentially of an infrequent cutter segment providing a recognition sequence for a sitespecific restriction enzyme, said recognition sequence being at least eight base pairs in length, and a discrete, hybridizable linker segment, said construct being adapted for insertion into a vector to provide a modified vector, each terminus of said linear oligonucleotide comprising a recognition sequence for a sitespecific restriction enzyme, whereby said construct is insertable into said vector, said linker segment being positioned intermediate said frequency cutter segment and said DNA molecule to be mapped and wherein the recognition sequence of each terminus is the same.

* * * * *